United States Patent
Yoo

[19]
[11] Patent Number: 6,083,591
[45] Date of Patent: Jul. 4, 2000

[54] MOXIBUSTING IMPLEMENT

[76] Inventor: Tae Woo Yoo, 807, 1-Dong, Hanyang, Apt. 32-5, Banpo-dong, Seocho-ku, Seoul, Rep. of Korea

[21] Appl. No.: 09/282,643

[22] Filed: Mar. 31, 1999

[30] Foreign Application Priority Data

Jan. 18, 1999 [KR] Rep. of Korea ............................ 99-464

[51] Int. Cl.[7] ................................. B32B 3/24; B32B 3/30
[52] U.S. Cl. ........................ 428/40.1; 428/66.6; 428/137; 428/172; 604/291
[58] Field of Search ................................. 428/40.1, 64.1, 428/66.6, 137, 172; 604/291, 24, 304

[56] References Cited

U.S. PATENT DOCUMENTS 5,549,960  8/1996  Yoo ......................................... 428/139

*Primary Examiner*—Alexander Thomas
*Attorney, Agent, or Firm*—Richard M. Goldberg

[57] ABSTRACT

A moxibusting implement includes a loess support having a centrally located receiving through hole and a cross-shaped air circulative groove at a lower surface thereof, the cross-shaped air circulative groove being in communication with the receiving hole in the loess support and extending from the receiving hole to an outer periphery of the loess support; a filter paper at the lower surface of the loess board; a paper board at a lower surface of the filter paper, the paper board having a receiving through hole therein which is co-axially aligned with the receiving hole in the loess support; an exfoliation paper at a lower surface of the paper board; and a cylindrical moxa at an upper surface of the loess support and having a hole which is co-axially aligned with the receiving hole in the loess support, the moxa being aligned with the receiving hole of the loess support, such that the moxibusting implement is capable of obtaining a wormwood effect and a strong and deep moxibusting effect by producing far-infrared radiation heat from the heated loess support and a sustained moxacautery effect by remaining heat after complete combustion, and such that environmental pollution is prevented due to perfect dissolution and oxidation.

7 Claims, 2 Drawing Sheets

MOXIBUSTING IMPLEMENT

BACKGROUND OF THE INVENTION

1. Field of the Invention

The present invention relates to a moxibusting implement and more particularly, to a moxibusting implement with sustained moxacautery without environmental pollution.

2. Description of the Prior Art

As shown in FIG. 4, the traditional moxibusting implement is manufactured by adhering an exfoliation paper (110) with a receiving hole (111) to a lower paper board (120) with a receiving hole (121). A filter paper (130) is then adhered to the lower paper board and an upper paper board (140) with a receiving hole (141) is adhered onto the filter paper in that order. Then a silver paper (150) with a receiving hole (151) is adhered to the upside of the upper paper board (140) and then a moxa (160) to the upside of the silver paper (150) in a regular sequence. The silver paper is adhered to the upside of the upper paper board in order to prevent the upper paper board (140) from igniting after a moxa (160) is completely burned. However, this implement has many problems in that the silver paper (150) is expensive and is neither burned up nor decays after use, which leads to environmental pollution. Also, since the moxibusting implement adheres the filter paper (130) between the upper paper board (140) and the lower paper board (120) by applying adhesives to both paper boards, the filter paper (130) can not perform its function practically due to the receiving holes of the filter paper being clogged by the adhesive. Especially, every receiving hole (151) (141) (121) formed in the silver paper (150) and the upper and lower paper boards (140), (120) is locked and incapable of performing an air circulation function because the lower paper board (120) is closely attached to the skin when the moxa (160) is oxidated. Moxacautery is performed not by the heated air and warmth flowing downwardly through the receiving holes (151) (141) (121), but by heating the environs of the affected part of a human body according to oxidating the moxa (160). The receiving holes (151) (141) (121) are locked as described above and moxa (160) makes much smoke according to a forced combustion. Therefore, it is difficult to take a breath in a closed space and a window should be open. When the moxa (160) is ignited, heat occurs from a point two-thirds of the way from the top. There are a lot of noneconomic problems, for instance, loss of heat, waste of moxa, dissatisfied moxacautery and so on.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENTS

Figure 1:
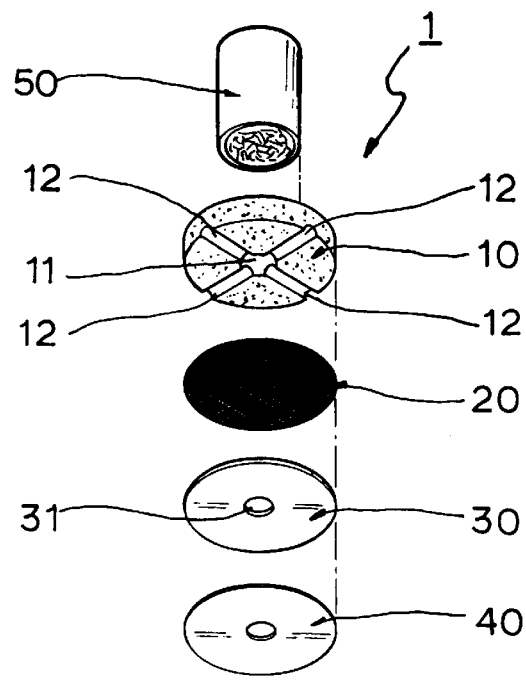
FIG. 1 is an exploded perspective view of a moxibusting implement according to the invention.
Figure 2:
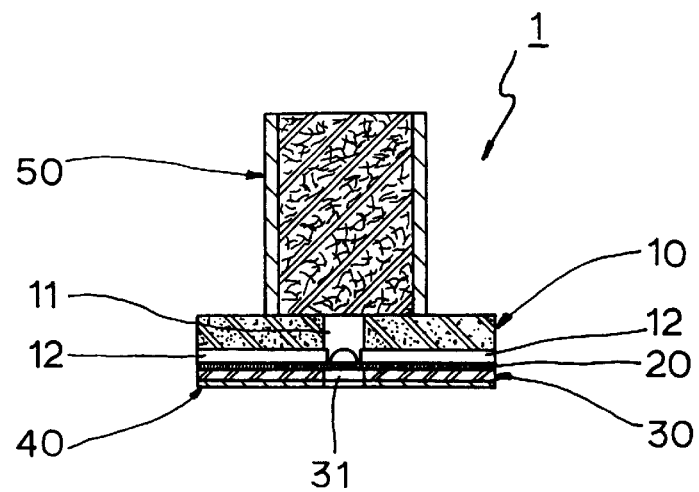
FIG. 2 is a cross-sectional view of a moxibusting implement according to the invention.

The moxibusting implement (1) according to the present invention is comprised of a loess support (10) having a small receiving hole (11) in the center and cross-shaped air circulative groove (12) at the bottom, a filter paper (20) at the lower part of the loess support (10), paper board (30) having a receiving hole (31), and an exfoliation paper (40), and a moxa (50) positioned on the upper part of the loess support (10).

Figure 3:
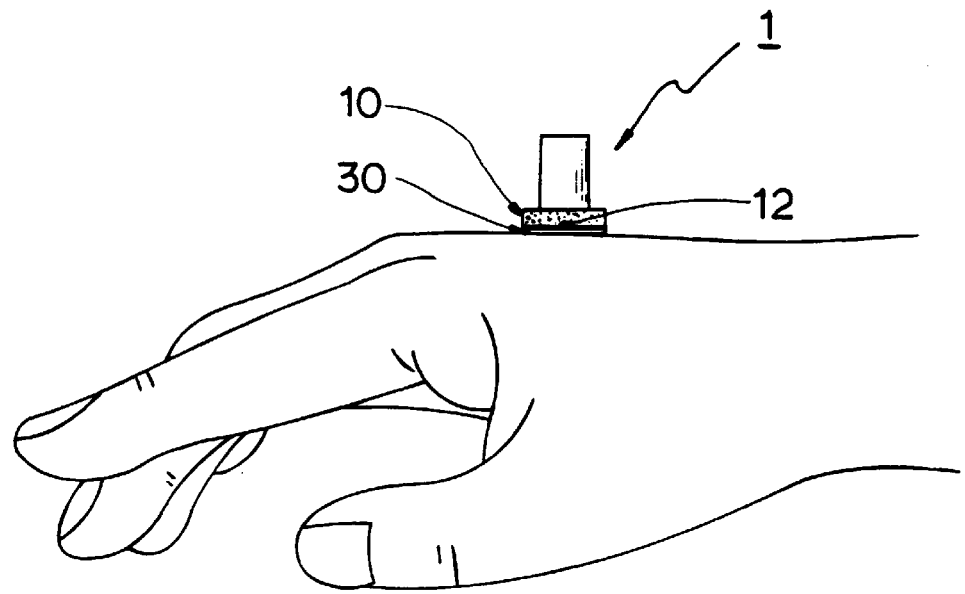
FIG. 3 is an illustrated view of the implement showing a state of operation.
Figure 4:
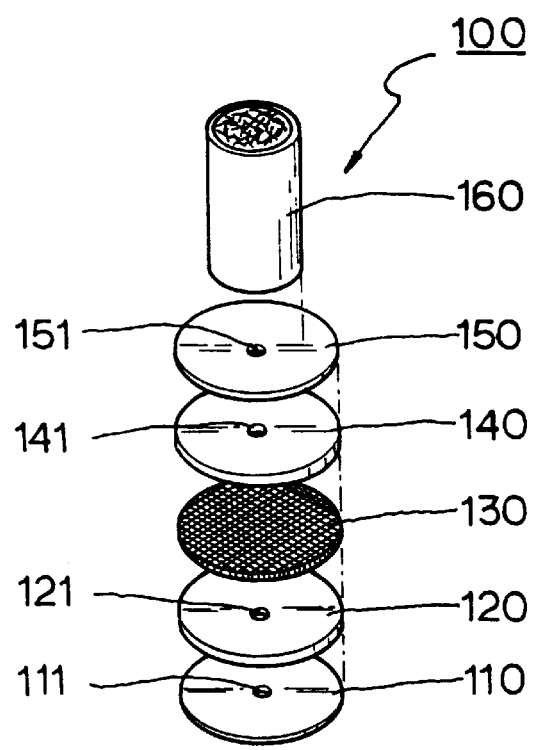
FIG. 4 is an exploded perspective view of a traditional moxibusting implement.

The present invention, the moxibusting implement (1) formed as above, is comprised of a small receiving hole (11) in the center so that heat may flow downwardly and the loess support (10) having the cross-shaped air circulative groove (12) at the bottom for air circulation, a filter paper (20) at the lower part of the loess support (10) for removing the remaining moxa at the lower part of the loess support (10), paper board (30) having a receiving hole (31), and an exfoliation paper (40), and a moxa (50) positioned on the upper part of the loess support (10). After removing the exfoliation paper (40) of the moxibusting implement (1) and adhering it at the skin surface as shown in FIG. 3, and then igniting the moxa (50), the moxa is oxidated and air is circulated smoothly through the cross-shaped air circulative groove (12) at the bottom of the loess support (10) and the occurring heat and smoke flow downwardly into each receiving hole (11) (31) without spreading smoke because the moxa (50) has a good combustibility. When the heat reaches the affected part, the remaining moxa is removed by the filter paper (20) and the loess board (10) is heated by the hot fever and far-infrared radiation is produced from the loess above a certain temperature. The effect of the moxacautery treatment is sustained by residual heat in the loess board (10) even after complete combustion of moxa (50). At the time of waste, the loess board (10) is completely dissolved and the paper board (30) is oxidated.

As mentioned above, the present invention provides a moxibusting implement (1) to enhance an effect of the moxacautery treatment by employing a cross-shaped air circulative groove (12) formed at the low part of the loess support (10) and improves air circulation smoothly. When a moxa (50) is ignited, the moxa (50) is oxidated and the heat goes through the small receiving hole (11) and filter paper (20) and is then inserted into the affected part through the receiving hole (31) of the paper board (30). At this moment, moxa resin is filtered by the filter paper (20) and the combustibility is better due to the continuous air circulation, smoke decreases and then the difficulty in taking a breath is overcome. The present invention has a strong moxibusting effect by producing far-infrared radiation heat and also, sustained moxacautery effect by heat remaining after complete combustion. The present invention provides an economical effect because there is no worry of ignition in the loess board (10) after the complete combustion and it is not necessary to use an expensive silver paper. The present invention also provides a sustained moxicautery effect even in a short time because the residual heat remains in the loess board (10) after a complete combustion, and therefore incapable of causing environmental pollution due to perfect dissolution and oxidation of the paper board (30).

What is claimed is:

1. A moxibusting implement comprising:

a loess support having a receiving hole in a center thereof and a cross-shaped air circulative groove at a lower surface thereof;

a filter paper at the lower surface of said loess board a paper board at a lower surface of said filter paper, said paper board having a receiving hole therein;

an exfoliation paper at a lower surface of said paper board; and a moxa at an upper surface of said loess support.

2. A moxibusting implement according to claim 1, wherein said receiving hole is a through hole located along a central axis of said loess support.

3. A moxibusting implement according to claim 1, wherein said receiving hole in said paper board is co-axially aligned with said receiving hole in said loess support.

4. A moxibusting implement according to claim 1, wherein said exfoliation paper has a hole which is co-axially aligned with said receiving hole in said loess support.

5. A moxibusting implement according to claim 1, wherein said moxa is aligned with said receiving hole of said loess support.

6. A moxibusting implement according to claim 5, wherein said receiving hole is a through hole located along a central axis of said loess support, and said moxa has a cylindrical configuration with a central axis in alignment with the receiving hole.

7. A moxibusting implement according to claim 1, wherein said cross-shaped air circulative groove is in communication with said receiving hole in said loess support, and extends from said receiving hole to an outer periphery of said loess support.

* * * * *